(12) United States Patent
Xu

(10) Patent No.: US 11,273,455 B2
(45) Date of Patent: Mar. 15, 2022

(54) METHOD OF DEWATERING POST FERMENTATION FLUIDS

(71) Applicant: NOVOZYMES A/S, Bagsvaerd (DK)

(72) Inventor: Feng Xu, Davis, CA (US)

(73) Assignee: NOVOZYMES A/S, Bagsvaerd (DK)

( * ) Notice: Subject to any disclaimer, the term of this patent is extended or adjusted under 35 U.S.C. 154(b) by 451 days.

(21) Appl. No.: 16/312,469

(22) PCT Filed: Jun. 8, 2017

(86) PCT No.: PCT/US2017/036490
§ 371 (c)(1),
(2) Date: Dec. 21, 2018

(87) PCT Pub. No.: WO2018/005035
PCT Pub. Date: Jan. 4, 2018

(65) Prior Publication Data
US 2019/0126293 A1    May 2, 2019

Related U.S. Application Data

(60) Provisional application No. 62/354,903, filed on Jun. 27, 2016.

(51) Int. Cl.
| | | |
|---|---|---|
| *B04B 1/20* | (2006.01) | |
| *C12N 9/22* | (2006.01) | |
| *C12P 7/10* | (2006.01) | |
| *C12N 1/20* | (2006.01) | |
| *B04B 3/04* | (2006.01) | |
| *B04B 5/10* | (2006.01) | |
| *C12R 1/10* | (2006.01) | |
| *C12R 1/125* | (2006.01) | |

(52) U.S. Cl.
CPC .............. *B04B 1/20* (2013.01); *B04B 3/04* (2013.01); *B04B 5/10* (2013.01); *C12N 1/205* (2021.05); *C12N 9/22* (2013.01); *C12P 7/10* (2013.01); *C12R 2001/10* (2021.05); *C12R 2001/125* (2021.05); *Y02E 50/10* (2013.01)

(58) Field of Classification Search
CPC combination set(s) only.
See application file for complete search history.

(56) References Cited

U.S. PATENT DOCUMENTS 8,962,268 B2 *  2/2015  De Wijn ........... G01N 33/57423
                                                    435/7.92
2005/0079270 A1   4/2005  Scheimann

FOREIGN PATENT DOCUMENTS

| WO | 2012/084225 A1 | 6/2012 |
| WO | 2013/096707 A1 | 6/2013 |
| WO | 2016/089816 A1 | 6/2016 |

OTHER PUBLICATIONS

Lu et al., 2016, Biotechnology for biofuels 9(1), 1-14.

* cited by examiner

*Primary Examiner* — Heidi Reese
(74) *Attorney, Agent, or Firm* — David Fazzolare

(57) ABSTRACT

The present invention relates to a method of dewatering post fermentation fluids in a starch to ethanol process. More particularly the invention relates to use of a nuclease enzyme for separation of whole stillage into an insoluble fraction and a supernatant fraction. In a specific embodiment the present invention relates to a method of dewatering whole stillage comprising the steps of: i) subjecting whole stillage to one or more nuclease enzymes; ii) separating the material into an insoluble fraction and a supernatant fraction.

19 Claims, No Drawings
Specification includes a Sequence Listing.

METHOD OF DEWATERING POST FERMENTATION FLUIDS

CROSS-REFERENCE TO RELATED APPLICATIONS

This application is a 35 U.S.C. 371 national application of international application no. PCT/US2017/036490 filed Jun. 8, 2017, which claims priority or the benefit under 35 U.S.C. 119 of U.S. application No. 62/354,903, filed Jun. 27, 2016, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to methods for enzymatic dewatering insolubles in pre- or post-fermentation fluids or streams.

BACKGROUND OF THE INVENTION

Fermentation products, such as ethanol, are produced by first degrading starch-containing material into fermentable sugars by liquefaction and saccharification and then converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining faction, referred to as "whole stillage" (WS), is dewatered and separated into a wet pellet (insoluble or "solid") and a supernatant ("liquid") phase, e.g., by centrifugation. The solid phase is referred to as "wet cake" (or "wet distiller's grains" (WDG)) and the liquid phase is referred to as "thin stillage". Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset" (B). Condensate may either be forwarded to a methanator before being discharged or may be recycled to the slurry tank. The syrup consisting mainly of limit dextrins and non-fermentable sugars may be blended into DDG or added to the wet cake before drying to produce DDGS (Distillers Dried Grain with Solubles).

US patent application no. 2005/0079270 A1 discloses a method of dewatering corn stillage solids comprising adding to the solids an anionic copolymer comprising acrylic acid sodium salt, meth acrylic acid sodium salt or 2-acrylamido-2-methyl-1-propanesulfonic acid sodium salt to form a mixture of water and coagulated and flocculated solids; and separating the water from the coagulated and flocculated solids using a dewatering device.

Dewatering of whole stillage or other post-fermentation fluids is energy demanding and may consume up to one-third or higher of the energy requirement of a plant producing ethanol or a similar fermentation product. The energy uses are inversely correlated to the hydration capacity of the solubles and insolubles in WS. Thus, there is a need for improving processes involved in dewatering of whole stillage and it is of interest to explore enzymatic dehydration ('dewatering') of post-fermentation fluids, so that their processing may use less energy. Similar enzymatic dehydrations may be applied to other pre- or post-fermentation fluids (streams) of corn ethanol production or other crop processing's, such as the steep liquor of corn wet milling.

SUMMARY OF THE INVENTION

The invention provides in a first aspect an enzymatic method of dewatering the whole stillage comprising the steps of
i) subjecting whole stillage to one or more nuclease enzymes;
ii) separating the material into an insoluble fraction and a supernatant fraction.

In a second aspect the present invention relates to a use of a nuclease enzyme for separation of whole stillage into an insoluble fraction and a supernatant fraction.

In a third aspect the present invention relates to a use of a nuclease enzyme for dewatering insolubles in pre- or post-fermentation fluids or streams apart from whole stillage

DETAILED DESCRIPTION OF THE INVENTION

Description of the Invention

The object of the present invention is to provide an enzymatic method of dewatering whole stillage.

The present inventors have surprisingly found that subjecting whole stillage to nuclease (DNAse, or phosphodiesterase) enzymes improves the solid-liquid separation and thereby decreases the water content in the wet cake after centrifugation compared to a corresponding method carried out without the presence of enzyme. Enzymes used for degrading whole stillage components include nucleases, carbohydrases such as alpha-amylase, glucoamylase, cellulase and/or hemicellulase, such as xylanase and beta-glucanase, pectinase, esterase, and protease, or a mixture thereof. Examples 3-5 show that subjecting whole stillage to one or more nucleases decreases the percentage of water in wet cake after centrifugation. This is advantageous as the energy cost of drying the wet cake is reduced when producing DDG or DDGS. The cost of transporting the wet cake from one place to another is also reduced. Further, the need for maintenance and repair of centrifuges, dryers and other equipment used is also reduced. All in all, the production cost is reduced.

Therefore, the first aspect the invention relates to a method of dewatering whole stillage comprising the steps of:
i) subjecting whole stillage to one or more nuclease enzymes,
ii) separating the material into an insoluble (wet cake) fraction and a supernatant (thin stillage) fraction.

Step i) and ii) may be carried out simultaneously or sequentially.

Whole Stillage and Production of Fermentation Products

The method of the invention may be used on whole stillage derived from production of any suitable fermentation product, preferably a liquid fermentation product. The feedstock for producing the fermentation product may be any starch-containing material, preferably starch-containing plant material, including: tubers, roots, whole grain; and any combination thereof. The starch-containing material may be obtained from cereals. Suitable starch-containing material includes corn (maize), wheat, barley, cassava, sorghum, rye, potato, or any combination thereof. Corn is the preferred feedstock, especially when the fermentation product is ethanol. The starch-containing material may also consist of or comprise, e.g., a side stream from starch processing, e.g., $C_6$ carbohydrate containing process streams that may not be suited for production of syrups. Whole stillage typically contains about 10-15 wt-% dry solids. Whole stillage components include fiber, hull, germ, oil, nucleic acid, and protein components from the starch-containing feedstock and fermenting microorganisms.

Production of a fermentation product is typically divided into the following main process stages:

a) Reducing the particle size of starch-containing material and pre-separation of certain components, e.g., by dry or wet milling;

b) Cooking the starch-containing material in aqueous slurry to gelatinize the starch, c) Liquefying the gelatinized starch-containing material in order to break down the starch (by hydrolysis) into maltodextrins (dextrins);

d) Saccharifying the maltodextrins (dextrins) to produce low molecular sugars (e.g., $DP_{1-2}$) that can be metabolized by a fermenting organism;

e) Fermenting the saccharified material using a suitable fermenting organism directly or indirectly converting low molecular sugars into the desired fermentation product;

f) Recovering the fermentation product, e.g., by distillation in order to separate the fermentation product from the fermentation mash, recovering or recycling various co-, by-, or side-products, such as stillage or steep liquor As also explained in the "Background"-section above whole stillage is a by-product consisting of liquids and solids remaining after recovery (e.g. by distillation) of a desired fermentation product from fermented mash (beer mash). According to the invention the fermentation product may be any fermentation product, including alcohols (e.g., ethanol, methanol, butanol, 1,3-propanediol); organic acids (e.g., citric acid, acetic acid, itaconic acid, lactic acid, gluconic acid, gluconate, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones. Fermentation is also commonly used in the consumable alcohol (e.g., beer and wine), dairy (e.g., in the production of yogurt and cheese), leather, and tobacco industries. In a preferred embodiment the fermentation product is a liquid, preferably an alcohol, especially ethanol.

The whole stillage contemplated according to the invention may be the side-product resulting from a fermentation product production process including above mentioned steps a) to f). However, the whole stillage may also be the side-product resulting from other fermentation product production processes based on starch-containing starting material.

Dewatering of Whole Stillage

Dewatering of whole stillage, in order to remove a significant portion of the liquid/water, may according to the invention (step ii) be done using any suitable separation technique, including centrifugation, pressing and filtration. In an embodiment the whole stillage is heated to a temperature of about 20-60° C. or around the optimum of the enzyme(s) in question. The pH is the range from 3-10, preferably pH 4-7, or around the optimum of the enzyme(s) in question. In general the enzymatic treatment of whole stillage is carried out under condition suitable for the enzyme(s) in question.

In a preferred embodiment the dewatering is carried out by centrifugation. Preferred centrifuges in industry today are decanter type centrifuges, preferably high speed decanter type centrifuges. An example of a suitable centrifuge is the NX 400 steep cone series from Alfa Laval which is a high-performance decanter.

In another preferred embodiment, the separation is carried out using other conventional separation equipment such as a plate/frame filter press, belt filter press, screw press, gravity thickeners and deckers, or similar equipment.

Drying of Wet Cake

After the wet cake, containing about 30-35 wt-% dry solids, has been dewatered it may be dried in a drum dryer, spray dryer, ring drier, fluid bed drier or the like in order to produce DDG. DDG is a valuable feed ingredient for livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake (insoluble fraction) is preferably dried under conditions that do not denature proteins in the wet cake. The wet cake may be blended with syrup separated from the thin stillage fraction and dried into DDGS.

The nuclease enzymes applied in step (i) of the method of the invention are in one embodiment selected from (a) phosphodiesterase, (b) polynucleotidase or nucleodepolymerase, (c) endonuclease or exonuclease, or (d) DNAse or RNAse.

More particularly the nuclease enzyme used in step i) is selected from the group consisting of members of EC 3.1.11.- (such as EC 3.1.11.1 to 6), EC 3.1.12.-, EC 3.1.13.-, EC 3.1.14.-, EC 3.1.15.-, EC 3.1.16.-, EC 3.1.21.- (such as EC 3.1.21.1 to 4), EC 3.1.22.-, EC 3.1.25.-, EC 3.1.26.-, EC 3.1.27.-, EC 3.1.3.-, EC 3.1.30.-, EC 3.1.31.-, EC 3.1.4.-, EC 3.1.99.-, family or a mixture thereof.

Nuclease enzyme may be derived from any suitable source. In a particular embodiment the nuclease enzyme is derived from a bacterium, e.g., *Bacillus*, such as *B. subtilis* or *B. licheniformis*, or from a fungus, e.g., *Aspergillus*, such as *A. oryzae*, or from a plant, e.g., mung bean, or from an animal source, e.g., bovine spleen.

In further aspects, the present invention also relates to a use of a nuclease enzyme for separation of whole stillage into an insoluble fraction and a supernatant fraction.

In particular, the separation may be done by centrifugation or filtration.

Apart from the applying the nucleases enzyme in dewatering of whole stillage it is also envisioned to use nuclease treatment for dewatering insolubles in pre- or post-fermentation fluids or streams apart from whole stillage.

The present invention is further disclosed in the below list of preferred embodiments.

Embodiment 1

A method of dewatering whole stillage comprising the steps of:
i) subjecting whole stillage to one or more nuclease enzymes;
ii) separating the material into an insoluble fraction and a supernatant fraction.

Embodiment 2

The method of embodiment 1, wherein step i) and ii) are carried out simultaneously or sequentially.

Embodiment 3

The method of embodiments 1 or 2, further comprising a step iii) of drying the insoluble fraction.

Embodiment 4

The method of any of embodiments 1-3, wherein separation in step ii) is carried out by centrifugation, preferably a decanter centrifuge.

Embodiment 5

The method of any of embodiments 1-3, wherein separation in step ii) is carried out by filtration, preferably using a filter press, a screw press, a plate-and-frame press, a gravity thickener or decker.

Embodiment 6

The method of any of embodiments 1-5, wherein step i) is carried out at a temperature in the range from 20-60° C.

Embodiment 7

The method of any of embodiments 1-6, wherein step i) is carried out at a pH in the range from 3-10, preferably 4-7.

Embodiment 8

The method of any of embodiments 1-7, wherein the whole stillage is derived from a process of producing a fermentation product, preferably a liquid fermentation product.

Embodiment 9

The method of any of embodiments 1-8, wherein the whole stillage is derive from a process of producing a fermentation product from starch-containing material.

Embodiment 10

The method of embodiment 9, wherein the starch-containing material is a cereal.

Embodiment 11

The method of embodiments 9, wherein the starch-containing material is selected from the group consisting of corn, wheat, barley, cassava, sorghum, rye, potato, or any combination thereof.

Embodiment 12

The method of embodiment 11, wherein the starch-containing material is corn.

Embodiment 13

The method of any of embodiments 8-12, wherein the fermentation product is an alcohol, preferably ethanol.

Embodiment 14

The method of any of embodiments 1-13, wherein the nuclease enzyme(s) used in step i) is(are) (a) phosphodiesterase, (b) polynucleotidase or nucleodepolymerase, (c) endonuclease or exonuclease, (d) DNAse or RNAse.

Embodiment 15

The method of any of embodiments 1-14, wherein the nuclease enzyme used in step i) is selected from the group consisting of members of EC 3.1.11.- (such as EC 3.1.11.1 to 6), EC 3.1.12.-, EC 3.1.13.-, EC 3.1.14.-, EC 3.1.15.-, EC 3.1.16.-, EC 3.1.21.- (such as EC 3.1.21.1 to 4), EC 3.1.22.-, EC 3.1.25.-, EC 3.1.26.-, EC 3.1.27.-, EC 3.1.3.-, EC 3.1.30.-, EC 3.1.31.-, EC 3.1.4.-, EC 3.1.99.-, family or a mixture thereof.

Embodiment 16

The method of embodiment 15, wherein the nuclease enzyme is derived from a bacterium, e.g., *Bacillus*, such as *B. subtilis* or *B. licheniformis*, or from a fungus, e.g., *Aspergillus*, such as *A. oryzae*, or from a plant, e.g., mung bean, or from an animal source, e.g., bovine spleen.

Embodiment 17

A use of a nuclease enzyme for separation of whole stillage into an insoluble fraction and a supernatant fraction.

Embodiment 18

The use of embodiment 17, wherein the separation is done by centrifugation or filtration.

Embodiment 19

A use of nuclease treatment for dewatering insolubles in pre- or post-fermentation fluids or streams apart from whole stillage.

The present invention is further illustrated in the following examples.

EXAMPLES

Example 1: Methods of Evaluating the Dewatering of the Insolubles in the Post-Fermentation Fluids The extent of hydration of the insolubles in the post-fermentation fluids (suspensions) was evaluated according to the procedures described below.

Post-fermentation fluids, including whole stillages (obtained after ethanol distillation from the fermented materials) and backsets (obtained after partial removal of the insolubles from whole stillages) were sampled from seven dry milling corn ethanol plants. They were measured for pH with a Beckman φ32 pH meter and a Thermo Scientific Orion 8175BNWP glass pH electrode, as well as dried matters (non-volatiles) content with a Denver Instruments IR60 moisture analyzer set at 130° C.

The weight of the original and treated whole stillages, backsets, centrifuged wet pellets, and supernatants are measured with a Mettler AB204-S balance, in polypropylene tubes by weight differences. Changes in levels of centrifuged wet pellets, equal to the ratios of the pellets' weight over the suspensions' weights, are used to evaluate the (de)hydration of the insolubles.

One mL of whole stillage or backset are pipetted into pre-weighed 1.7-mL microcentrifuge tubes, and the tubes with the samples are weighed. The tubes are centrifuged at 21130 g for 5 minutes. The supernatants are pipetted into other pre-weighed 1.7-mL microcentrifuge tubes, and the tubes with the supernatants are weighed. The tubes with the centrifuged pellets are weighed. The supernatants are pipetted back to the pellets to reconstitute the whole stillage or backset suspensions, and the tubes with the reconstituted suspensions are weighed. The net weights of the suspensions, supernatants, and pellets, as well as the pellet level as w % of the suspensions, are calculated from these weighing results. The loss from pipetting transfer of the supernatants is (0.17±0.04)%.

Example 2: Preparation of Nuclease Polypeptides

*Aspergillus oryzae* Nuc A/B polypeptide (disclosed as SEQ ID NO: 1 and the mature polypeptide disclosed as SEQ ID NO: 2) may be prepared as described in WO2015155350. *Bacillus licheniformis* Nuc B polypeptide (SEQ ID NO: 5 and the mature polypeptide SEQ ID NO: 6) may be produced as disclosed in WO2011098579.

*Bacillus subtilis* Nuc B polypeptide (SEQ ID NO: 3 and the mature polypeptide of SEQ ID NO: 4) has previously been disclosed, e.g., in WO2014081884 and WO2014087011 and may be prepared according to known methods in the art.

Example 3: Effect of Mixture of Nuclease Polypeptides on the Pellets of Whole Stillage or Backset The effect of *A. oryzae*, *B. licheniformis*, and *B. subtilis* nuclease polypeptides on the relative weight of the pellet to that of the whole stillage or backset was determined as described below.

Mixtures of the three nuclease peptides were applied at 0, 1.0 (0.33 for each), and 10.0 (3.3 for each) mg/L levels to the whole stillages and backsets, and the capped reaction tubes were gently shaken (on a rocking platform at 1.5 rpm) at room temperature (23° C.). After 4 and 27 hours, the weights of the reaction suspensions, centrifuged pellets and supernatants were determined as described in Example 1. The pellet levels relative to the values before the reaction started were determined as a dehydration measurement.

Various extents of decrease in the pellet level were observed when the nucleases were reacted with various whole stillages and backsets, at two different doses and under two different times. Table 1 lists the data for the whole stillage #3 and backset #7. The decrease in pellet level is attributable to dehydration of the pellets by the nucleases.

TABLE 1

| | Nuclease mix, mg/L | Pellet level relative to pre-reaction level | |
|---|---|---|---|
| | | 4 hours of reaction | 27 hours of reaction |
| Whole stillage #3 | 0 | 0.94 | 0.96 |
| | 1 | 0.89 | 0.88 |
| | 10 | 0.85 | 0.84 |

TABLE 1-continued

| | Nuclease mix, mg/L | Pellet level relative to pre-reaction level | |
|---|---|---|---|
| | | 4 hours of reaction | 27 hours of reaction |
| Backset #7 | 0 | 1.13 | 1.05 |
| | 1 | 0.97 | 0.92 |
| | 10 | 1.00 | 0.92 |

Example 4: Effect of Nuclease Polypeptides on the Pellets of Whole Stillage

The effects of *A. oryzae*, *B. licheniformis*, and *B. subtilis* nuclease polypeptides on the relative weight of the pellet to that of the whole stillage or backset were determined similarly as described in Example 3, except the modifications noted below.

The nuclease peptides were applied individually at 0, 1, and 10 mg/L levels to the whole stillage #3, and the reactions were carried out for 5 and 71 hours. The pellet levels after 71 hours of reaction were compared to the values after 5 hours of reaction, as a dehydration measurement.

Various extents of decrease in the pellet level were observed when the nucleases were reacted with the whole stillage.

TABLE 2

| Nuclease | Nuclease, mg/L | 71-hour pellet level relative to 5-hour level |
|---|---|---|
| None | 0 | 1.01 |
| *A. oryzae* | 1 | 0.96 |
| SEQ ID NO: 2 | 10 | 1.00 |
| *B. licheniformis* | 1 | 0.96 |
| SEQ ID NO: 6 | 10 | 0.93 |
| *B. subtilis* | 1 | 0.96 |
| SEQ ID NO: 4 | 10 | 0.93 |

Example 5: Effect of Nuclease Polypeptides on the Pellets of Whole Stillage

The effects of *A. oryzae*, *B. licheniformis*, and *B. subtilis* nuclease polypeptides on the relative weight of the pellet to that of the whole stillage or backset were determined similarly as described in Examples 3 and 4, except the modifications noted below.

The nuclease peptides were applied individually at 0, 1, and 10 mg/L levels to the whole stillage #3, as well as in mixtures at 3 (1 for each) and 30 (10 for each) mg/L. The reactions were carried out for 4 and 27 hours. The pellet levels relative to the values before the reaction started were determined as a dehydration measurement.

Various extents of decrease in the pellet level were observed when the nucleases were reacted with the whole stillage. As shown in Table 3, the *B. subtilis* nuclease was more active than the *B. licheniformis* and *A. oryzae* nuclease in decreasing the pellet level, and contributed the most to the activity of the nuclease mixtures.

TABLE 3

| Nuclease | Nuclease, mg/L | Pellet level relative to pre-reaction level | |
|---|---|---|---|
| | | 4 hours of reaction | 27 hours of reaction |
| None | 0 | 0.93 | 0.92 |
| A. oryzae | 1 | 0.94 | 0.94 |
| | 10 | 0.93 | 0.92 |
| B. licheniformis | 1 | 0.90 | 0.93 |
| | 10 | 0.88 | 0.90 |
| B. subtilis | 1 | 0.91 | 0.89 |
| | 10 | 0.86 | 0.85 |
| Mixture (1:1:1) | 3 | 0.86 | 0.86 |
| | 30 | 0.85 | 0.84 |

The overall results demonstrated that nuclease polypeptide could decrease the pellet level in whole stillage and backset, indicating the dehydration of the pellet.

The invention described and claimed herein is not to be limited in scope by the specific aspects herein disclosed, since these aspects are intended as illustrations of several aspects of the invention. Any equivalent aspects are intended to be within the scope of this invention. In-deed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method of dewatering whole stillage comprising the steps of:
    i) subjecting whole stillage to one or more nuclease enzymes;
    ii) separating the material into an insoluble fraction and a supernatant fraction.

2. The method of claim 1, wherein separation in step ii) is carried out by centrifugation.

3. The method of claim 1, wherein separation in step ii) is carried out by filtration.

4. The method of claim 1, wherein the whole stillage is derived from a process of producing a fermentation product.

5. The method of claim 1, wherein the whole stillage is derived from a process of producing a fermentation product from starch-containing material.

6. The method of claim 5, wherein the starch-containing material is a cereal.

7. The method of claims 5, wherein the starch-containing material is selected from the group consisting of corn, wheat, barley, cassava, sorghum, rye and potato, or any combination thereof.

8. The method of claim 7, wherein the starch-containing material is corn.

9. The method of claim 4, wherein the fermentation product is an alcohol.

10. The method of claim 1, wherein the nuclease enzyme(s) used in step i) is(are): (a) phosphodiesterase, (b) polynucleotidase or nucleodepolymerase, (c) endonuclease or exonuclease, or (d) DNAse or RNAse.

11. The method of claim 1, wherein the nuclease enzyme used in step i) is selected from the group consisting of members of EC 3.1.11.-, EC 3.1.12.-, EC 3.1.13.-, EC 3.1.14.-, EC 3.1.15.-, EC 3.1.16.-, EC 3.1.21.- (such as EC 3.1.21.1 to 4), EC 3.1.22.-, EC 3.1.25.-, EC 3.1.26.-, EC 3.1.27.-, EC 3.1.3.-, EC 3.1.30.-, EC 3.1.31.-, EC 3.1.4.- and EC 3.1.99.-, family, or a mixture thereof.

12. The method of claim 11, wherein the nuclease enzyme is derived from a bacterium.

13. The method of claim 4, wherein the fermentation product is ethanol.

14. The method of claim 12, wherein the bacterium is a strain of *Bacillus*.

15. The method of claim 14, wherein the strain is selected from the group consisting of *B. subtilis* and *B licheniformis*.

16. The method of claim 12, wherein the fungus is a strain of *Aspergillus*.

17. The method of claim 16, wherein the strain is *A. oryzae*.

18. The method of claim 12, wherein the plant is mung bean.

19. The method of claim 12, wherein the animal source is bovine spleen.

* * * * *

UNITED STATES PATENT AND TRADEMARK OFFICE
CERTIFICATE OF CORRECTION

PATENT NO. : 11,273,455 B2
APPLICATION NO. : 16/312469
DATED : March 15, 2022
INVENTOR(S) : Xu et al.

It is certified that error appears in the above-identified patent and that said Letters Patent is hereby corrected as shown below:

In the Claims

Please amend Claim 12 (Column 16, Lines 31-32) as follows:
12. The method of claim 11, wherein the nuclease enzyme is derived from a bacterium, a fungus, a plant, or an animal source.

Signed and Sealed this
Thirteenth Day of June, 2023

*Katherine Kelly Vidal*

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 243
<212> TYPE: PRT
<213> ORGANISM: Aspergillus oryzae

<400> SEQUENCE: 1

Met Gln Leu Thr Lys Ser Leu Leu Val Phe Ala Leu Tyr Met Phe Gly
1               5                   10                  15

Thr Gln His Val Leu Ala Val Pro Val Asn Pro Glu Pro Asp Ala Thr
                20                  25                  30

Ser Val Glu Asn Val Ala Leu Lys Thr Gly Ser Gly Asp Ser Gln Ser
            35                  40                  45

Asp Pro Ile Lys Ala Asp Leu Glu Val Lys Gly Gln Ser Ala Leu Pro
        50                  55                  60

Phe Asp Val Asp Cys Trp Ala Ile Leu Cys Lys Gly Ala Pro Asn Val
65                  70                  75                  80

Leu Gln Arg Val Asn Glu Lys Thr Lys Asn Ser Asn Arg Asp Arg Ser
                85                  90                  95

Gly Ala Asn Lys Gly Pro Phe Lys Asp Pro Gln Lys Trp Gly Ile Lys
            100                 105                 110

Ala Leu Pro Pro Lys Asn Pro Ser Trp Ser Ala Gln Asp Phe Lys Ser
        115                 120                 125

Pro Glu Glu Tyr Ala Phe Ala Ser Ser Leu Gln Gly Gly Thr Asn Ala
    130                 135                 140

Ile Leu Ala Pro Val Asn Leu Ala Ser Gln Asn Ser Gln Gly Gly Val
145                 150                 155                 160

Leu Asn Gly Phe Tyr Ser Ala Asn Lys Val Ala Gln Phe Asp Pro Ser
                165                 170                 175

Lys Pro Gln Gln Thr Lys Gly Thr Trp Phe Gln Ile Thr Lys Phe Thr
            180                 185                 190

Gly Ala Ala Gly Pro Tyr Cys Lys Ala Leu Gly Ser Asn Asp Lys Ser
        195                 200                 205

Val Cys Asp Lys Asn Lys Asn Ile Ala Gly Asp Trp Gly Phe Asp Pro
    210                 215                 220

Ala Lys Trp Ala Tyr Gln Tyr Asp Glu Lys Asn Asn Lys Phe Asn Tyr
225                 230                 235                 240

Val Gly Lys

<210> SEQ ID NO 2
```

<211> LENGTH: 221
<212> TYPE: PRT
<213> ORGANISM: Aspergillus oryzae

<400> SEQUENCE: 2

Val Pro Val Asn Pro Glu Pro Asp Ala Thr Ser Val Glu Asn Val Ala
1               5                   10                  15

Leu Lys Thr Gly Ser Gly Asp Ser Gln Ser Asp Pro Ile Lys Ala Asp
            20                  25                  30

Leu Glu Val Lys Gly Gln Ser Ala Leu Pro Phe Asp Val Asp Cys Trp
        35                  40                  45

Ala Ile Leu Cys Lys Gly Ala Pro Asn Val Leu Gln Arg Val Asn Glu
50                  55                  60

Lys Thr Lys Asn Ser Asn Arg Asp Arg Ser Gly Ala Asn Lys Gly Pro
65                  70                  75                  80

Phe Lys Asp Pro Gln Lys Trp Gly Ile Lys Ala Leu Pro Pro Lys Asn
                85                  90                  95

Pro Ser Trp Ser Ala Gln Asp Phe Lys Ser Pro Glu Glu Tyr Ala Phe
            100                 105                 110

Ala Ser Ser Leu Gln Gly Gly Thr Asn Ala Ile Leu Ala Pro Val Asn
        115                 120                 125

Leu Ala Ser Gln Asn Ser Gln Gly Gly Val Leu Asn Gly Phe Tyr Ser
130                 135                 140

Ala Asn Lys Val Ala Gln Phe Asp Pro Ser Lys Pro Gln Thr Lys
145                 150                 155                 160

Gly Thr Trp Phe Gln Ile Thr Lys Phe Thr Gly Ala Ala Gly Pro Tyr
                165                 170                 175

Cys Lys Ala Leu Gly Ser Asn Asp Lys Ser Val Cys Asp Lys Asn Lys
            180                 185                 190

Asn Ile Ala Gly Asp Trp Gly Phe Asp Pro Ala Lys Trp Ala Tyr Gln
        195                 200                 205

Tyr Asp Glu Lys Asn Asn Lys Phe Asn Tyr Val Gly Lys
210                 215                 220

<210> SEQ ID NO 3
<211> LENGTH: 136
<212> TYPE: PRT
<213> ORGANISM: Bacillus subtilis

<400> SEQUENCE: 3

Met Lys Lys Trp Met Ala Gly Leu Phe Leu Ala Ala Val Leu Leu
1               5                   10                  15

Cys Leu Met Val Pro Gln Gln Ile Gln Gly Ala Ser Ser Tyr Asp Lys
            20                  25                  30

Val Leu Tyr Phe Pro Leu Ser Arg Tyr Pro Glu Thr Gly Ser His Ile
        35                  40                  45

Arg Asp Ala Ile Ala Glu Gly His Pro Asp Ile Cys Thr Ile Asp Arg
50                  55                  60

Asp Gly Ala Asp Lys Arg Arg Glu Glu Ser Leu Lys Gly Ile Pro Thr
65                  70                  75                  80

Lys Pro Gly Tyr Asp Arg Asp Glu Trp Pro Met Ala Val Cys Glu Glu
                85                  90                  95

Gly Gly Ala Gly Ala Asp Val Arg Tyr Val Thr Pro Ser Asp Asn Arg
            100                 105                 110

Gly Ala Gly Ser Trp Val Gly Asn Gln Met Ser Ser Tyr Pro Asp Gly
        115                 120                 125

Thr Arg Val Leu Phe Ile Val Gln
            130                 135

<210> SEQ ID NO 4
<211> LENGTH: 110
<212> TYPE: PRT
<213> ORGANISM: Bacillus subtilis

<400> SEQUENCE: 4

Ala Ser Ser Tyr Asp Lys Val Leu Tyr Phe Pro Leu Ser Arg Tyr Pro
1               5                   10                  15

Glu Thr Gly Ser His Ile Arg Asp Ala Ile Ala Glu Gly His Pro Asp
            20                  25                  30

Ile Cys Thr Ile Asp Arg Asp Gly Ala Asp Lys Arg Arg Glu Glu Ser
        35                  40                  45

Leu Lys Gly Ile Pro Thr Lys Pro Gly Tyr Asp Arg Asp Glu Trp Pro
    50                  55                  60

Met Ala Val Cys Glu Glu Gly Gly Ala Gly Ala Asp Val Arg Tyr Val
65                  70                  75                  80

Thr Pro Ser Asp Asn Arg Gly Ala Gly Ser Trp Val Gly Asn Gln Met
                85                  90                  95

Ser Ser Tyr Pro Asp Gly Thr Arg Val Leu Phe Ile Val Gln
            100                 105                 110

<210> SEQ ID NO 5
<211> LENGTH: 142
<212> TYPE: PRT
<213> ORGANISM: Bacillus licheniformis

<400> SEQUENCE: 5

Met Ile Lys Lys Trp Ala Val His Leu Leu Phe Ser Ala Leu Val Leu
1               5                   10                  15

Leu Gly Leu Ser Gly Gly Ala Ala Tyr Ser Pro Gln His Ala Glu Gly
            20                  25                  30

Ala Ala Arg Tyr Asp Asp Ile Leu Tyr Phe Pro Ala Ser Arg Tyr Pro
        35                  40                  45

Glu Thr Gly Ala His Ile Ser Asp Ala Ile Lys Ala Gly His Ser Asp
    50                  55                  60

Val Cys Thr Ile Glu Arg Ser Gly Ala Asp Lys Arg Arg Gln Glu Ser
65                  70                  75                  80

Leu Lys Gly Ile Pro Thr Lys Pro Gly Phe Asp Arg Asp Glu Trp Pro
                85                  90                  95

Met Ala Met Cys Glu Glu Gly Gly Lys Gly Ala Ser Val Arg Tyr Val
            100                 105                 110

Ser Ser Ser Asp Asn Arg Gly Ala Gly Ser Trp Val Gly Asn Arg Leu
        115                 120                 125

Ser Gly Phe Ala Asp Gly Thr Arg Ile Leu Phe Ile Val Gln
    130                 135                 140

<210> SEQ ID NO 6
<211> LENGTH: 118
<212> TYPE: PRT
<213> ORGANISM: Bacillus licheniformis

<400> SEQUENCE: 6

Tyr Ser Pro Gln His Ala Glu Gly Ala Ala Arg Tyr Asp Asp Ile Leu
1               5                   10                  15

-continued

```
Tyr Phe Pro Ala Ser Arg Tyr Pro Glu Thr Gly Ala His Ile Ser Asp
            20              25              30

Ala Ile Lys Ala Gly His Ser Asp Val Cys Thr Ile Glu Arg Ser Gly
        35              40              45

Ala Asp Lys Arg Arg Gln Glu Ser Leu Lys Gly Ile Pro Thr Lys Pro
        50              55              60

Gly Phe Asp Arg Asp Glu Trp Pro Met Ala Met Cys Glu Glu Gly Gly
65              70              75              80

Lys Gly Ala Ser Val Arg Tyr Val Ser Ser Ser Asp Asn Arg Gly Ala
            85              90              95

Gly Ser Trp Val Gly Asn Arg Leu Ser Gly Phe Ala Asp Gly Thr Arg
            100             105             110

Ile Leu Phe Ile Val Gln
            115
```